United States Patent [19]

Mason

[11] Patent Number: 4,925,645
[45] Date of Patent: May 15, 1990

[54] METHOD OF PREPARING A MIXTURE OF CHLORINE CONTAINING SUBSTANCES INCLUDING CHLORINE DIOXIDE

[76] Inventor: James A. Mason, P.O. Box 605, Theodore, Ala. 36590

[21] Appl. No.: 253,852

[22] Filed: Oct. 5, 1988

[51] Int. Cl.$^5$ .............................................. C01B 11/02
[52] U.S. Cl. .................................................... 423/477
[58] Field of Search ........................................ 423/477

[56] References Cited

U.S. PATENT DOCUMENTS 4,084,747  4/1978  Alliger ................................ 423/477

FOREIGN PATENT DOCUMENTS 959238  12/1974  Canada ................................ 423/477

Primary Examiner—Jeffrey E. Russel
Attorney, Agent, or Firm—George L. Williamson

[57] ABSTRACT

The present invention describes a novel method of producing an aqueous solution containing chlorine dioxide. The mixture is produced by mixing an organic hydroxy acid or carboxylic acid, an alkali metal chlorite or alkaline earth metal chlorite and water in specified steps. Very high concentrations of chlorine dioxide may be produced by the method.

For example, lactic acid is added to water to form a first solution and mixed. Sodium chlorite is then added to the first solution to form a second solution and mixed resulting in an aqueous solution of chlorine containing substances including chlorine dioxide.

9 Claims, No Drawings

METHOD OF PREPARING A MIXTURE OF CHLORINE CONTAINING SUBSTANCES INCLUDING CHLORINE DIOXIDE

BACKGROUND OF THE INVENTION

This invention generally relates to a method of production of a mixture of chlorine containing substances in concentrations suitable for use as an oxidizing agent in various industrial processes. Exemplary industrial processes where chlorine containing substances may be used as an oxidizing agent or disinfectant include the disinfection of water and wastewater to destroy bacteria and/or pathogens, as a whitening agent in the paper industry and for water treatment in the oil recovery industry.

More particularly, the present invention provides for a method of preparing a mixture of chlorine containing substances wherein chlorine dioxide is one of the substances present in high concentrations. It is believed that the other chlorine containing substances included in the mixture include chlorous acid, chloric acid and chlorine.

Methods and/or apparatuses for preparing chlorine containing substances including chlorine dioxide have been described in the prior art. Ratigan, in U.S. Pat. No. 4,250,144, described a generating system for chlorine dioxide for use in the water or wastewater treatment industry. Ward et al in U.S. Pat. No. 4,013,761, described an invention for generating chlorine dioxide including a generation vessel having leak inhibiting solvent weld joints with reducing couplings. Hartshorn, in U.S. Pat. No. 4,104,190, described a system of generating chlorine dioxide from aqueous liquids containing alkali metal or alkaline earth metal chlorites, and compounds which liberate chlorine in water. Rapson et al, in U.S. Pat. No. 4,534,952, described a small scaled generator of chlorine dioxide for water treatment. Rosenblatt et al, in U.S. Pat. No. 4,504,442, described a use of chlorine dioxide gas as a chemosterilizing agent particularly involving gas impermeable surfaces of implements commonly employed in the medical sciences. Callerami, in U.S. Pat. No. 3,754,079, described a process of preparing chlorine dioxide for use in the bleaching of wood pulp, fats, oils and flour. Capuano et al, in U.S. Pat. No. 4,542,008, described an electro-chemical process for producing chlorine dioxide from an aqueous solution of sodium chlorite. Hicks, in U.S. Pat. No. 4,590,057, described a process for the generation of chlorine dioxide from an aqueous solution of a metal chlorite and an oxidizing agent, preferably gaseous chlorine.

However, none of the prior art cited above discloses the unique method of preparing a mixture of chlorine containing substances including chlorine dioxide as disclosed by the present invention.

SUMMARY OF THE INVENTION

According to the invention there is provided a method of forming chlorine dioxide and other chlorine containing compounds and/or substances in an aqueous solution from the reaction of lactic acid or citric acid with sodium chlorite to yield a salt of the acid and chlorous acid. This is the first reaction suspected in a series of reactions leading to the production of chlorine dioxide and is more particularly accomplished by introducing the lactic acid into water first and then mixing the contents of the reaction vessel by stirring. After the lactic acid and water are thoroughly mixed, the sodium chlorite is added to the mixture and again mixed by stirring. This reaction is carried out at atmospheric pressure, at a pH<7 and at a temperature of <120° F., generally in the range of approximately 60° F. to 80° F., most preferably about 62° F. The aqueous solution containing chlorine dioxide formed from the aforementioned reaction and subsequent reactions is relatively chemically stable and can be safely transported by common carrier, e.g., drums, tank truck or railway tank car, to the plant site for use.

It is believed that the aforementioned reaction is the first of a chain of reactions leading to the production of chlorine dioxide. These further reactions, generally, involve the oxidation of various organic or inorganic compounds or destruction of pathogens by either chlorous acid, chloric acid, chlorine dioxide or chlorine or a mixture of these substances and will be further described by use of chemical equations in the following section of this specification. The kinetics of these reactions are complex but it is believed that the reactions may occur more or less simultaneously with varying concentrations of the reaction and products being present as the reactions proceed to completion.

The chlorine containing compounds produced by the present invention are intended for use as a bactericide to inhibit the growth of bacteria found in water and/or wastewater in order to make it potable or to disinfect it as the case may be. It is also intended to remove color, odor and taste problems that may be present in the water and/or wastewater. For example, such problems may be caused by algae, phenoles and/or the presence of hydrogen sulfide. A particular advantage of the present invention is that the production of trihalomethane, other undesirable polychlorinated hydrocarbons such as dioxin, chlorates and chlorites are minimized and/or eliminated. Other uses of the products of the present invention have been previously mentioned, e.g., as a bleaching agent in the paper industry and for water treatment in the oil recovery industry.

Note that it may be feasible to substitute other alkali metal or alkaline earth metal chlorites for sodium chlorite sometimes referred to in this specification. Also note, that it may be feasible to substitute other acids, such as citric, tartaric, malic and glycolic acids and/or other organic hydroxy acids and carboxylic acids for lactic acid.

One of the primary objectives and advantages of the present invention is that it allows for the formation of a relatively chemically stable mixture containing chlorine dioxide in an aqueous solution using bulk quantity reactants which allows for the production of the chlorine dioxide off site rather than on-site at a particular industrial site. Off site production is important because it allows for a much safer generating process for chlorine dioxide whereby the risk of fire and explosion are minimized. It is anticipated that the aqueous mixture containing chlorine dioxide would be shipped to the plant site by, e.g., tank truck or railway tank car. Furthermore, the present invention allows for the mixing and formation of the chlorine dioxide in an aqueous solution involving bulk quantities and mixing ratios which are extremely simple and basic whereby more or less generally lesser-trained personnel can accomplish the production of the chlorine dioxide. This method allows for the delivery of a source of chlorine dioxide to a plant site by merely transporting an aqueous solution, e.g., by a cool or a refrigerated means which is not now done because chlorine dioxide can not be safely transported and therefore is now generally generated on-site.

centration of chlorine dioxide produced by these reactions. The 26% by volume of sodium chlorite and 88% by volume of lactic acid are commonly commercially

Best Mode for Carrying Out the Invention

A more detailed description of the present invention follows in the form of chemical equations and examples.
The reactions utilized in the method of the present invention are as follows:

1. $CH_3CH(OH)COOH + NaClO_2 \longrightarrow CH_3CH(OH)COONa + HClO_2$
   (lactic acid) (sodium chlorite) (salt of lactic acid) (chlorous acid)

Citric acid, $HOC(CH_2COOH)_2COOH$, may be substituted for Lactic Acid. Also, malic, tartaric and glycolic acid may be substituted for lactic acid.

2. a. $HClO_2 +$ Non Fully Oxidized Organics $\longrightarrow HClO +$ Oxidized Organics
   (chlorous acid)    or Inorganics                         or Inorganics
                                                            (Hypochlorus acid)

2. b. $2HClO_2 \longrightarrow HClO + HClO_3$
   (chlorous acid) (Hypochlorus acid) (chloric acid)

(This reaction occurs in absence of chloride ion)
This reaction 2.b. is not desirable, but it will occur simultaneously with reaction 3., but not necessarily at the same rate.

3. $HClO + 2HClO_2 \longrightarrow 2ClO_2 + H_2O + HCl$ (This reaction occurs in absence of chloride ion)

4. $ClO_2 +$ Non Fully $\longrightarrow HClO_2 +$ Oxidized Organics or Inorganics
           Oxidized Organics
           or Inorganics Reaction 3. provides chloride ions, therefore the following reaction occurs:

5. $HClO + Cl^- + H^+ \rightleftharpoons Cl_2 + H_2O$

The Chlorine reaction with organics or Inorganics is generally thought to be primarily an Oxidation as follows:

6. $Cl_2 +$ Organics or Inorganics $\longrightarrow$ Oxidized Organics or Inorganics The above reactions are carried out at atmospheric prssure and at a pH less than 7. These reactions result in a relative chemically stable mixture of chlorine dioxide in an aqueous solution.

It is believed that the powerful oxidation and/or disinfection nature and characteristic of the present invention is due to the action of chlorous acid, chloric acid, chlorine dioxide or chlorine, either jointly or singularly, or, a mixture of these chemical substances.

In practice, the reactants and reactions are produced by mixing bulk quantities of water, sodium chlorite and lactic acid to form an aqueous solution. In practice, about 1 part of lactic acid at a concentration of about 88% by volume, which is a food grade of lactic acid, is mixed with about 51 parts water and then mixed thoroughly by stirring. About three parts of sodium chlorite at a concentration of about 25–26% by volume is then added to this solution and again mixed. In practice, the water could vary from about 49–53 parts, the lactic acid could vary from about 0.8–1.2 parts and the sodium chlorite could vary from about 2.5–3.5 parts. Variations in the proportions or ratios of reactants in the ranges specified above results in variations in the concentrations of the end products of the reactions, e.g., the concentration of chlorine dioxide produced by these reactions. The 26% by volume of sodium chlorite and 88% by volume of lactic acid are commonly commercially available bulk quantities of these compounds and are generally provided to industry commercially in either drum lots or bulk quantities, for example, tank cars or tank trucks. Furthermore, note in the above reaction Number 1. that citric acid, $HOC(CH_2COOH)_2COOH$, at a concentration of about 55% by volume may be substituted for the lactic acid to produce a salt of citric acid and chlorous acid in an aqueous solution by using slightly different mixing ratios.

The above reactions are accomplished by mixing the reactants together at atmospheric pressure in an aqueous solution with the water temperature being less than 120° F., preferably in the range of about 60° F. to 80° F., most preferably about 62° F. The higher water temperatures nearing 80° F. can be used if necessary to increase the reaction speed. Higher water temperatures may be feasible.

Explaining in more detail, small quantities may be obtained by the simple process of introducing into a small reaction vessel, (vessel should be one impervious to oxidents, such as chlorine, $ClO_2$, etc.) about 51 parts water, about 1 part 88% Lactic Acid food or technical grade, and about 3 parts 25% Sodium Chlorite. The Lactic Acid should be introduced into the water first, then mixed by stirring. After the water and Lactic Acid are thoroughly mixed add Sodium Chlorite and stir rapidly to obtain the final mixture. The water used should be at a temperature of not more than about 120° F., preferably between about 60° F.–80° F., and most preferably about 62° F. The temperature of water will determine the reaction time required for the desired results. Higher water temperatures of course, result in more rapid formation of the end products. The final result being a mixture of $HClO_2$, $HClO_3$, $ClO_2$ and $Cl_2$ in various concentrations, with the $ClO_2$ being at approximately 5000 ppm, using about 51 parts water, about one part lactic acid and about three parts sodium chlorite. Mixtures of about 4000 ppm to about 6000 ppm $ClO_2$ commonly occur in these solutions.

This mixture should immediately be transferred by pouring into a container impervious to the product, and capped tightly. It then may be stored at temperatures not to exceed 80° F. for long and possibly indefinite lengths of time. Lab tests have indicated that storage of up to 8 months is possible with little loss of initial strength. Lab tests have indicated that solutions made by mixing different organic acids including lactic acid, citric acid, malic acid and tartaric acid with sodium chlorite retained their concentrations within 2% plus or minus for at least 30 days.

If larger quantities are desired such as 55 gal. drum lots, similar steps are used. The drum should generally be a commercially available unit polyethelyene lined, using about 51 gals. water, about 1 gal. Lactic Acid, and about 3 gals. Sodium Chlorite in the following order. Fill the drum to ½ to ¾ capacity with water, i.e. about 28–38 gallons, add Lactic Acid, mixing thoroughly by stirring or agitation with, for example, a small commercially available agitator. Add the Sodium Chlorite and fill drum to capacity with additional water. Cap tightly immediately and store at below 80° F. About the same concentration of product i.e., about 5000 ppm, as explained above are obtained. The drum can then be shipped to the end use site but steps should be taken to insure that it is not exposed to temperatures in excess of 90° F. for extended times.

If tank car quantities are required, the same steps should be taken, except use a larger lined steel, stainless steel, polyethylene, or fiber glass tank equipped with an electrically powered agitator. If a 6000 gal shipment is desired for example use the same ratio of about 51 parts water, about 1 part Lactic Acid, and about 3 parts Sodium Chlorite. Add approximately ⅔ of the total required water to the tank. Engage agitator pump, add Lactic Acid, allow to mix approximately 5 minutes, then leaving agitator engaged, add Sodium Chlorite and the balance of water to total about 51 parts required water. Transfer the mixture immediately to sealed commercial truck tanks suitable for transportation of this type product. Again, care must be taken to limit the maximum temperature for prolonged periods of time. Refrigerated units are commercially available to meet this requirement.

If the product is to be produced in very large quantities for immediate use such as in the bleaching of paper, flour, etc., the warmer water temperatures may be necessary to obtain a more rapid reaction. Otherwise no particular emphasis should be placed on water temperature, and, tap water temperatures are acceptable within the limits herein described.

The ratio used in these examples result in a product strength of about 5000 ppm $ClO_2$. Stronger mixtures may be readily and safely obtained by changing these ratios of reactants. For example, to obtain a $ClO_2$ strength of approximately 15,000 ppm your ratio should be:

about 45 parts water
about 2½ parts Lactic Acid
about 7½ parts Sodium Chlorite

Higher strengths in excess of 100,000 ppm may be obtained. If this is desired more care should be taken to keep the final resulting product at below about 50° F. until it is introduced into the desired end use.

Please note that the mixing order of reactants must be carefully observed. If not, a violent reaction may result. It is believed that this is caused by the Lactic Acid being or different liquid consistancy and/or density than the other constituents.

The aqueous solution resulting from the reactions above has a density of about 1.0039, a boiling point of about 101.6° C., a freezing point of about $-3°$ C. and a pH of approximately 4.7. The solution is completely miscible in water, has a pungent odor resembling chlorine and a color of clear to slightly amber.

As can be seen, the results of the present invention can be accomplished by easily mixing on a part to part basis commonly available commercial products in bulk quantities so as to produce the desired reactions. Granulated sodium chlorite can also be used to make up the bulk quantity of this aqueous solution.

The above reactions produce aqueous solutions containing very high concentrations of chlorine dioxide ranging from generally about 5000 ppm to about 80,000 ppm. Furthermore, the chlorine dioxide produced by the present invention appears to have more oxidizing and pathogen destroying power on a per unit basis than chlorine dioxide produced by other methods. It is believed that his is due to the fact that the chlorine is available in the form of various substances including chlorous acid, chloric acid, chlorine dioxide and chlorine.

The invention will now be described by several examples, it being understood, however, that these examples are given by way of illustration and not by way of limitation in that many changes may be effected without affecting in anyway the scope and spirit of this invention as recited in the appended claims.

EXAMPLE 1

The reaction was carried out using one 55 gallon drum by volume of lactic acid at 88%, i.e., food grade, and three 55 gallon drums of 26% sodium chlorite by volume to yield the desired reactions.

The lactic acid and sodium chlorite were first mixed in a large vessel of water having a temperature of approximately 62° F. being at atmospheric pressure.

EXAMPLE 2

A granulated Sodium Chlorite was dissolved in water to form a 48% sodium chlorite solution according to standard published data on solubility of Sodium Chlorite. This solution was then combined with a solution of 88% lactic acid. An immediate reaction occurred forming a deep brown solution. This solution was tested and the presence of $ClO_2$ was detected. No attempt was made to ascertain the concentration of $ClO_2$ ppm in this solution.

EXAMPLE 3

The same steps were taken as in Example 2 using 2 parts sodium chlorite, 1 part lactic acid, 4 parts water at approximately 60° F. Again the reaction showed the presence of $ClO_2$ after reaction in a closed vessel for approximately 30 minutes.

EXAMPLE 4

The same steps were used as in Example 3 except the water was heated to a maximum temperature of approximately 120° F. The reaction appeared to take place much faster.

EXAMPLE 5

A commercially available 26% solution of sodium chlorite was used with 88% lactic acid solution on a one to one basis. The same reaction was observed as in Example 2.

EXAMPLE 6

Same as example 5, except 2 parts sodium chlorite 26% to 1 part lactic acid to 10 parts water at approximately 60° F. This formed a solution containing chlorine Dioxide in excess of 80,000 ppm according to accepted tests.

EXAMPLE 7

Same as example 6, except 2-½ parts of sodium chlorite 26% was used to 1 part lactic acid to 10 parts water at approximately 60° F. with approximately the same results as Example 6.

EXAMPLE 8

Same as Example 7, except 3 parts sodium chlorite 26% to 1 part lactic acid 88% to 50 parts water at 60° F. This solution formed a solution containing 5000 plus or minus ppm $ClO_2$.

EXAMPLE 9

A storage test was conducted where solutions were placed in 12 oz. amber bottles and capped. ⅓ were stored out of sunlight at approximately 72° F., ⅓ placed outside was exposed to sunlight and varying temperatures. ⅓ was placed in refrigerator at approximately 38° F.

Tests were conducted to determine loss of concentration and as expected the solution placed outdoors was the most unstable. The solution at 72° retained its concentration to within 2% plus or minus for at least 60 days at which time tests were discontinued.

The refrigerated solutions tested the same as the ones stored at 72° indoors, and were retained up to 120 days at which time sample tests were discontinued.

EXAMPLE 10

Tests were conducted to determine if larger quantities could be commercially produced.

3 gals of 26% sodium chlorite, 1 gal of 88% lactic acid, 51 gals water in 55 gal drums, were combined using the following steps; (1) a 55 gal. drum was filled approximately ⅓ full with water and 1 gal 88% lactic acid added and agitated to mix; (2) 3 gals 26% sodium chlorite added and agitated; (3) drum was then filled with water and capped for 15 minutes; (4) drum uncapped and tested and found to contain $ClO_2$ at 5000 ppm plus or minus 2%.

EXAMPLE 11

Same as Example 10 except 6 gal/sodium chlorite, 2 gals/lactic acid and 47 gals/water were combined to produce a solution containing 10,000+ ppm $ClO_2$.

EXAMPLE 12

Same as Example 10 except 8 gals/sodium chloride, 2½ gals/lactic acid, 44½ gal/water were combined. Test showed 18,000 plus or minus 2% ppm $ClO_2$.

It was found that a solution of 10,000 ppm may be stored in drums without loss of appreciable concentrations up to 90 days.

EXAMPLE 13

Tests were conducted in a Northwest Florida potable surface water treatment facility. The facility treats an average of 16 MGD. A 55 gal drum of approximate 5000 ppm $ClO_2$ solution was used and fed into the system prior to flocculation, at a rate of 1 gal. solution per million gal. water.

Samples were taken and tested on site and also by a certified water testing laboratory in N.W. Florida. The results showed 0 total coliforms, trihalomethane production was below detection level, and no chlorites or chlorates were detectable in the samples taken.

It is believed that the most desirable concentration for the treatment of potable water is about 5000 ppm $ClO_2$ due to ease of handling and effectiveness of product as a disinfectant.

EXAMPLE 14

Grab samples were taken from a large Southwestern city potable (surface water) water filtration system. The samples were treated by applying 5000 ppm $ClO_2$ solution to the water in the following part to part ratios: ½ gal. solution per million gals. water; 1 gal. solution per million gals. water; and, 2 gal. solution per million gals. water.

The results were the same as in Example 13 when mixing 2 gal. solution per million gals. water.

EXAMPLE 15

Grab samples were taken from a South Alabama municipal potable (surface water) and treated the same as in Example 13, with the same results as Example 13.

EXAMPLE 16

Tests were conducted in a small South Louisiana city. Groundwater is pumped from a depth in excess of 1500 feet. 5 wells supply the city's total water requirements. High concentrations of $H_2S$ as evidenced by the strong sulfur taste and rotten egg smell. The $H_2S$ levels tested to show 5 ppm. A 55 gal. drum of 5000 ppm $ClO_2$ solution was delivered to each well location and applied to the raw water at each wellhead at a rate of 1 part solution per M.G.D. Samples of water at each location were taken periodically over a period of 30 days. Results showed complete elimination of $H_2S$ taste and odor. Tests by a certified laboratory in South Louisiana showed no adverse effects in final treated water.

I claim:

1. A process for producing a mixture containing chlorine dioxide comprising the steps of:
   (a) forming a first solution by introducing an organic acid into water in a reaction vessel said organic acid being selected from the group consisting of lactic acid or citric acid;

(b) mixing said first solution by stirring;

(c) thereafter forming a second solution by introducing sodium chlorite into said first solution following said mixing;

(d) mixing said second solution by stirring; and (e) storing said stirred second solution containing chlorine dioxide at temperatures not exceeding 80° F. wherein the chlorine dioxide is stable and maintains its original concentration within 2% of its original value for at least 30 days.

2. A process as claimed in claim 1, wherein the acid is citric acid.

3. A process as claimed in claim 2, wherein the water temperature has a range of about 60° F. to about 80° F.

4. A process as claimed in claim 3, wherein the water temperature is approximately 62° F.

5. The process of claim 1, wherein the organic acid is lactic acid.

6. A process as claimed in claim 5, wherein a total of about 49 to about 53 parts water by volume, about 0.8 to about 1.2 parts lactic acid by volume and about 2.5 to about 3.5 parts sodium chlorite by volume are used.

7. A process as claimed in claim 6, wherein the water temperature ranges from about 60° F. to about 80° F.

8. The process of claim 7, wherein the water temperature is approximately 62° F.

9. A process as claimed in claim 6, wherein chlorine dioxide is formed having a concentration varying from about 4000 to about 6000 parts per million.

* * * * *